United States Patent
Livesley et al.

[11] Patent Number: 5,976,436
[45] Date of Patent: Nov. 2, 1999

[54] PROCESS FOR PRODUCTION OF MEDICAMENT FORMULATIONS

[75] Inventors: David J Livesley, Elsworth; Ian M D Gaylor, Ely, both of United Kingdom

[73] Assignee: Fisons plc, Suffolk, United Kingdom

[21] Appl. No.: 08/821,383

[22] Filed: Mar. 20, 1997

Related U.S. Application Data

[63] Continuation of application No. 08/351,247, filed as application No. PCT/GB93/01375, Jun. 30, 1993, abandoned.

[30] Foreign Application Priority Data

Jun. 30, 1992 [GB] United Kingdom ................... 9213874

[51] Int. Cl.$^6$ ............................ A61K 9/72; A61M 15/00; B30B 5/02; B32B 31/14
[52] U.S. Cl. ......................... 264/113; 264/115; 264/122; 264/314; 100/211; 128/203.15; 425/389; 425/417; 425/DIG. 14; 425/DIG. 44
[58] Field of Search ..................................... 264/109, 314, 264/112, 115, 122, 113; 100/211, 212; 128/203.15, 203.28; 425/389, 393, 403, 417, 438, 441, 443, DIG. 14, DIG. 44; 424/46, 464, 467, 489, 468, 471

[56] References Cited

U.S. PATENT DOCUMENTS

| | | | |
|---|---|---|---|
| 950,567 | 3/1910 | Kesling | .................................... 425/417 |
| 2,312,381 | 3/1943 | Bickenheuser . | |
| 2,587,215 | 2/1952 | Priestly | .............................. 128/203.15 |
| 3,561,079 | 2/1971 | Anderson | .................................. 425/417 |
| 3,583,200 | 6/1971 | Cvijanovic | ....................... 425/DIG. 14 |
| 4,039,703 | 8/1977 | Kamijo et al. . | |
| 5,341,800 | 8/1994 | Clark et al. | ................................ 424/46 |
| 5,482,946 | 1/1996 | Clark et al. | .............................. 424/464 |
| 5,538,999 | 7/1996 | Clark et al. | .............................. 424/464 |

FOREIGN PATENT DOCUMENTS

| | | |
|---|---|---|
| 0 381 499 | 8/1990 | European Pat. Off. . |
| 0 407 028 A2 | 1/1991 | European Pat. Off. . |
| 1346567 | 11/1963 | France . |
| 881701 | 8/1960 | United Kingdom . |
| WO 91/03237 | 3/1991 | WIPO . |

OTHER PUBLICATIONS

Patent Abstracts of Japan, vol. 15 No. 203 (M–1116) May 24, 1991 & PJ A 30 55 206 (Taiyo Seimitsu KK) Mar. 11, 1991. See abstract.

*Primary Examiner*—Jan H. Silbaugh
*Assistant Examiner*—Kenneth M. Jones
*Attorney, Agent, or Firm*—Nixon & Vanderhye

[57] ABSTRACT

A process for the production of compacted bodies of powdered medicament is disclosed, the process comprising the steps of:
  a) positioning expansible means along the longitudinal axis of the mold;
  b) placing loose powdered medicament in the mold; and
  c) expanding the expansible means perpendicularly to the longitudinal axis of the mold. An apparatus for use in the process according to the invention and medicament compacts formed by the process are also disclosed.

36 Claims, 6 Drawing Sheets

PROCESS FOR PRODUCTION OF MEDICAMENT FORMULATIONS

This is a Rule 62 continuation of application Ser. No. 08/351,247, filed Dec. 7, 1994, now abandoned, which is a 376 of PCT/GB93/01375 filed Jun. 30, 1993.

This invention relates to a novel process for the production of a compacted body of powdered medicament, especially powdered inhalation medicament, referred to herein as a "medicament compact", of the type disclosed in European Patent Application 407028.

BACKGROUND OF THE INVENTION

The administration by inhalation of medicaments in dry powder form is well known. Devices for the metering and dispensing of measured doses of medicament from a reservoir have also been described previously, for example, in UK Patent No. 2041763 and U.S. Pat. No. 2587215. Such devices typically comprise a medicament reservoir and a metering chamber with a volume chosen such that, when filled, the chamber contains the desired weight of medicament for one dose. Filling of the metering chamber is generally accomplished under the influence of gravity, the chamber typically being located at the bottom of the reservoir. Such devices have the disadvantage that variations in the density of the metered powder can easily occur is resulting in inaccurate or inconsistent dosing. The packing density of the powder may also depend on the weight of powder remaining in the reservoir, leading to a gradual reduction in the dose delivered by the device. In addition, the dose metered is strongly dependent on the orientation of the device.

European Patent Application 407028 discloses a device which overcomes the disadvantages of other dry powder devices by the use of a metering means which relies not on gravitational force to fill a metering chamber, but on abrasion of a compacted body of powdered medicament. This application contemplated the use of hydraulic presses and the like in the production of the medicament compacts, by which pressure would be applied in the direction of a longitudinal axis of a sample of powdered medicament. Although this is satisfactory in many cases, in others there is a variation in the density of the medicament compact from point to point. Since the device of European Patent Application No. 407028 (in which the medicament compacts are adapted for use) functions by abrading a fixed volume of the medicament compact, it is important that the density of medicament throughout the compact is as uniform as possible. If the density is uniform then slices of medicament of the same thickness abraded from the compact will contain the same amount of medicament, thus ensuring that the correct dosage of medicament is consistently administered to a patient.

We have now found a novel process for the production of medicament compacts which overcomes or substantially mitigates the problems encountered in processes known from the prior art.

According to the present invention, there is provided a process for the production of a medicament compact, which comprises the steps of:

a) positioning expansible means along the longitudinal axis of a mould;

b) placing loose powdered medicament in the mould; and c) expanding the expansible means perpendicularly to the longitudinal axis of the mould.

Steps a) and b) may be performed in either order or simultaneously, however, we prefer them to be performed in the order shown above.

The powdered medicament is preferably metered into the mould, e.g. by weighing the desired amount of medicament. Alternatively, medicament compacts of the desired total mass may be produced by cutting to the appropriate length.

After performing steps a) and b), or during step b), it is preferable to vibrate the mould assembly and/or action a levelling device. This ensures that the medicament has settled to a level height i.e. that the top surface of the medicament is even, and is of known volume prior to compaction. Vibration of the mould assembly may achieved using the base unit of a vibratory bowl feeder, this provides axial vibration of adjustable amplitude.

During vibration of the mould assembly it is desirable that any loose parts of the assembly should be held in position, this may be accomplished by using a vacuum to hold such parts in place.

Suitable expansible means for use in the process according to the invention include an expansible mandrel, for example, a cylindrical mandrel capable of radial expansion. The cylindrical mandrel may comprise a plurality of segments capable of radial movement, in the retracted state the segments form a complete cylinder and in the expanded state gaps are present between the segments. The mandrel preferably has from 2 to 12, for example, 6 segments. When the medicament compact is to be administered from a device according to European Patent Application 407028 which, for a single dose, abrades a cylindrical compact for a predetermined angle of less than 360° around the longitudinal axis, then the mandrel preferably has the same number of segments as there are doses in a 360° rotation about the longitudinal axis of the compact. For example if the device abrades the compact for 60° about the longitudinal axis for a single dose then the expanding mandrel preferably has 6 segments. This minimises the effects of any irregularities in the internal configuration of the compact.

Outward radial movement of the segments may be produced by a wedging action using e.g. pistons and/or by inflation of a bag placed at the centre of the mandrel. Inflation of the bag may be achieved using compressed gas, e.g. air; or hydraulically.

The degree of expansion of the mandrel will depend upon the desired size and density of the medicament compact, for example, the mandrel may expand from a diameter of 16 mm to 20 mm.

The outer surface of the mandrel is preferably covered by an elastomeric sleeve. The sleeve prevents ingress of powder into the expansible means. The elastomeric sleeve may be made of any material which exhibits a suitable degree of elasticity, e.g. vulcanised rubber. In addition to a suitable degree of elasticity, the elastomeric material should be non-toxic and preferably has a high degree of tear resistance and is easily moulded. The elastomeric material is preferably a vulcanised elastomer suitable for is drug contact, for example, a natural rubber or silicone rubber compound.

As the elastomeric sleeve expands radially it's thickness reduces and there may be a tendency for it to shorten in length. It is desirable for the sleeve to remain a constant length, so it is preferable that the ends of the sleeve turn inwards towards the longitudinal axis of the mandrel. This may help to prevent axial shortening in two ways, firstly, it grips onto the ends of the mandrel segments, thus restricting shrinkage by shear forces; secondly, as it expands and its outer diameter increases, radial tension is generated which tries to pull the cylinder edges in towards the axis.

As the mandrel expands the elastomeric sleeve may tend to flatten across the gaps which open up between the segments. This effect may be reduced by applying a pressure, e.g. of 5 bar, to the interior of the elastoineric sleeve, thus allowing it to be inflated relative to the expansible means. At other times it is desirable to maintain a lower pressure, e.g. 0.5 bar, within the elastomeric sleeve, this pressure helps to prevent the ingress of powder into the expansible mandrel.

Other expansible means which may be mentioned include inflatable means such as inflatable bags, inflation of the bag may be achieved using compressed gas, e.g. air; or hydraulically.

The pressure exerted by the expansible means will depend upon the desired density of medicament in the compact (by density of medicament we mean the mass of medicament per unit volume). However, the expansible means typically exerts a pressure of from $60 \times 10^3$ to $2000 \times 10^3$ N.m$^{-2}$, for example $900 \times 10^3$ N.m$^{-2}$.

The density of the medicament in the compacts produced according to the invention will depend inter alia upon medicament used. However, a typical compact may have a density of from 0.1 to 1.5 g/cm$^3$, preferably from 0.4 to 0.8 g/cm$^3$. The density of the medicament compacts produced according to the invention may be determined by weighing a fixed volume of medicament abraded from the compact.

We prefer the medicament compact to be formed in a mould which subsequently forms all or part of the medicament reservoir of a medicament inhalation device. Thus, after compaction the compact and mould are in a form suitable for direct transfer to the inhalation device. By obviating the need to remove the compact from the mould prior to its insertion in the device, handling of the medicament compact, and hence the risk of contamination or loss of medicament through premature abrasion, is reduced.

After production the compact may be transferred directly to the inhalation device from which it is to be administered, alternatively the compacts may be packaged separately thus providing replacement indictment reservoirs for the device from which they are to be administered.

According to a second aspect, the invention provides the novel apparatus described herein for carrying out the first aspect of the invention.

Therefore we provide an apparatus for the production of a medicament compact from loose powdered medicament which comprises:

a) a mould having a longitudinal axis adapted to receive loose powdered medicament, b) expansible means adapted to be positioned along the longitudinal axis of the mould, and c) means for expanding the expansible means perpendicularly to the longitudinal axis of the mould.

The process according to the invention may further be combined with the axial compaction process envisaged in European Patent Application 407028, thus allowing the formation of compacted annuli one on top of the other. When axial compaction is used the process must also include rotation of the compact relative to the expansible means of the mould in order to release the compact from the mould.

The process of the invention has the advantage that it produces medicament compacts having a more uniform density than compacts produced by prior art processes. In particular the density of the material at a given radius from the longitudinal axis of the compact will be the same throughout the compact, although the density at different radii need not be the same, such medicament compacts are novel. Medicament compacts having such a density distribution are advantageous in that sequential volumes of medicament abraded from the compact, e.g. by the device disclosed in European Patent Application 407028, will have similar masses, thus resulting in improved uniformity of dose administered to the patient.

The process is also advantageous in that it allows medicament compacts to be produced in a single rather than a multi-step compaction procedure, it also allows the production of longer compacts having a more uniform density distribution. The process also ensures good adhesion of the medicament to the wall of the powder chamber, this is advantageous when the medicament is formed in a mould which subsequently form all or part of the medicament reservoir of an inhalation device since it prevents the compact slipping during abrasion.

According to further aspect of the invention we provide a compact of powdered inhalation medicament characterised in that the density at all points at a given radius from the longitudinal axis of the compact is substantially the same.

Furthermore, we provide a compact of powdered inhalation medicament, obtainable by a process comprising the steps of:

a) positioning expansible means along the longitudinal axis of a mould;

b) placing loose powdered medicament in the mould; and c) expanding the expansible means perpendicularly to the longitudinal axis of the mould.

Medicament compacts according to these further aspects of the invention will usually be annular, i.e. cylindrical with a cylindrical inner space. The radial thickness of the medicament in such a medicament compact is preferably in the range of 0.2 to 20 mm, more preferably 0.5 to 5 mm, for example 2 mm. The cylindrical inner space preferably has a diameter of more than 10 mm and preferably less than 100 mm, for example 20 mm.

The length of the medicament compact will depend on its intended use and the number of doses of active ingredient it contains. For administration from a device as disclosed in European Patent Application No. 407028, a suitable length will be in the range 5 to 50 mm, e.g. 20 mm.

Active ingredients which may be incorporated in compacts according to the invention include any active ingredients which are conventionally administered by inhalation in powdered form. Such active ingredients include drugs for use in the prophylactic or remedial treatment of reversible obstructive airways disease. Specific active ingredients which may be mentioned include salts of cromoglycic acid, e.g. sodium cromoglycate; salts of nedocromil, e.g. nedocromil sodium; inhaled steroids such as beclomethasone dipropionate, tipredane, budesonide and fluticasone; anticholinergic agents such as ipratropium bromide; bronchodilators, e.g. salmeterol, salbutamol, reproterol, terbutaline, isoprenaline and fenoterol, and salts thereof. If desired a mixture of active ingredients, for example, al mixture of sodium cromoglycate and a bronchodilator, such as salbutamol, reproterol, isoprenaline, terbutaline, fenoterol or a salt of any one thereof, may be used.

Other active ingredients that may be mentioned include antihistamines, e.g. clemastine, pentamidine and salts thereof, acetyl-β-methylcholine bromide; peptide hormones, e.g. insulin and amylin; bradykinin antagonists; PLA$_2$ inhibitors; PAF antagonists; lipoxygenase inhibitors; leukotriene antagonists; CNS active drugs, e.g. NMDA antagonists, glutamate antagonists, CCK agonists and antagonists; macrolide compounds, e.g. FK 506, rapamycini, cyclosporin ind structurally related compounds; vitamins; vaccines, e.g. MMR vaccine and polio vaccine; and vectors for gene therapy, e.g. plasmids containing genes intended to correct genetic disorders such as cystic fibrosis.

The particles of active ingredient incorporated into the medicament compacts according to the invention preferably have a mass median diameter in the range 0.01 to 15 μm. We prefer that at least 80% w/w and preferably at least 90% w/w of the particles of active ingredient are less than 20 μm, more preferably less than 10 μm, especially less than 7 μm in diameter. The proportion of particles of active ingredient having a diameter in the range 2 to 15 μm is preferably more than 80% w/w.

The particulate active ingredient may be prepared by any suitable technique, as will be known to those skilled in the art. Suitable techniques include milling, e.g. using a hammer or fluid energy mill, micronisation, spray drying and freeze drying.

The medicaments to be compacted according to the invention may comprise a solid pharmaceutically acceptable carrier substance in addition to an active ingredient. The carrier preferably has an effective particle size of from 10 to 100 μm.

The term "effective particle size" is used to denote the apparent particle size of a body without distinction as to the number of individual particles which go to make up that body i.e. no distinction is made between a single particle of given size and an agglomerate of the same size which is composed of finer individual particles.

The solid pharmaceutically acceptable carrier in the medicament will generally be a non-toxic material chemically inert to the active ingredient but may, if so desired, also comprise larger particles of the active ingredient. Examples of carriers which may be used in the medicament compacts include dextrans, glucose, mannitol and lactose. A particularly preferred carrier is crystalline lactose.

The particulate carrier may be prepared by grinding the carrier and subsequently separating out the desired fraction by conventional methods, e.g. by air classification and sieving.

The medicament may be prepared by mixing the ingredients together in a mixer, e.g. a planetary or other stirred mixer, prior to formation of the compact according to the process of the invention.

When the medicament comprises a solid carrier, we prefer the proportion of active ingredient to be from 0.1 to 70% w/w, more preferably from 0.1 to 55% w/w, and especially from 5 to 50% w/w of the medicament.

The medicament compacts according to the invention may also contain other ingredients such as flavouring agents, sweetening agents or colourants.

Any conventional pharmaceutically acceptable flavouring agents may be used, particular flavouring agents which may be mentioned include volatile oils, e.g. peppermint oil; and menthol. The proprietary product known by the tradename Dentomint, which contains both peppermint oil and menthol, may also be used. We prefer the flavouring agent to be peppermint oil BP/Ph. Eur.

We prefer the flavouring agent to be a polysaccharide entrapped flavouring agent such as those disclosed in Internationail Patent Application No. PCT/GB93/00503. Polysaccharide entrapped flavouring agents are advantageous for use in the compacts produced according to the invention since they are sufficiently resilient to sustain the compression forces required to produce the medicament compacts without releasing the flavouring agent entrapped therein to any significant extent.

Sweetening agents which may be used include any conventional sweetening agents, particular sweetening agents which may be mentioned include saccharin sodium, mannitol, aspartame, cyclamates and sugar.

The medicament compacts produced according to the invention preferably contain a plurality of doses of active ingredient. The actual number of doses incorporated into the compacts will depend inter alia upon the length of the compact, the nature of the active ingredient and the device from which it is to be administered. However, the compacts will typically comprises from 20 to 250, e.g. 112 doses of active ingredient.

EXAMPLES

The following noii-limitative examples illustrate medicament compositions suitable for use in the process according to the invention:

| Ingredients | % w/w |
| --- | --- |
| Example 1 | |
| Nedocromil sodium (milled) | 50 |
| Flavoured polysaccharide | 5 |
| (85% maltodextrin:15% peppermint oil) | |
| Lactose | to 100 |
| Example 2 | |
| Nedocromil sodium (milled) | 50 |
| Flavoured polysaccharide | 5 |
| (85% maltodextrin:15% peppermint oil) | |
| Saccharin sodium | 1.25 |
| Lactose | to 100 |
| Example 3 | |
| Tipredane (micronised) | 10 |
| Lactose | to 100 |

The process of the invention may be adapted to form medicament compacts comprising concentric annuli of different drugs and/or carrier substances. The process may use any number of different expansible means to achieve the desired combination of densities and annular thickness. A compact suitable for the administration of a combination drug therapy may therefore comprise a first annulus of active ingredient A, an intermediate annulus of a carrier substance, e.g. lactose, and a final annulus of active ingredient B; the intermediate annulus of carrier substance serving to separate the two active ingredients thus preventing unwanted interactions which may occur during storage. Combination drug therapy compacts may contain, for example, a mixture of sodium cromoglycate and a bronchodilator, such as salbutamol or reproterol.

The shape of the expansible means may also be changed so as to form annuli of different configurations, for example, with internal spaces of elliptical cross section. The internal walls of the compact may also be tapered, thereby forming medicament compacts in which the dose of medicament is gradually increased or decreased as subsequent doses are administered. As a further alternative medicament compacts comprising radial segments of different drugs and/or carrier substances may be produced.

BRIEF DESCRIPTION OF THE DRAWINGS

The invention will now be described, by way of example only, with reference to the accompanying drawings, in which.

Figure 1:
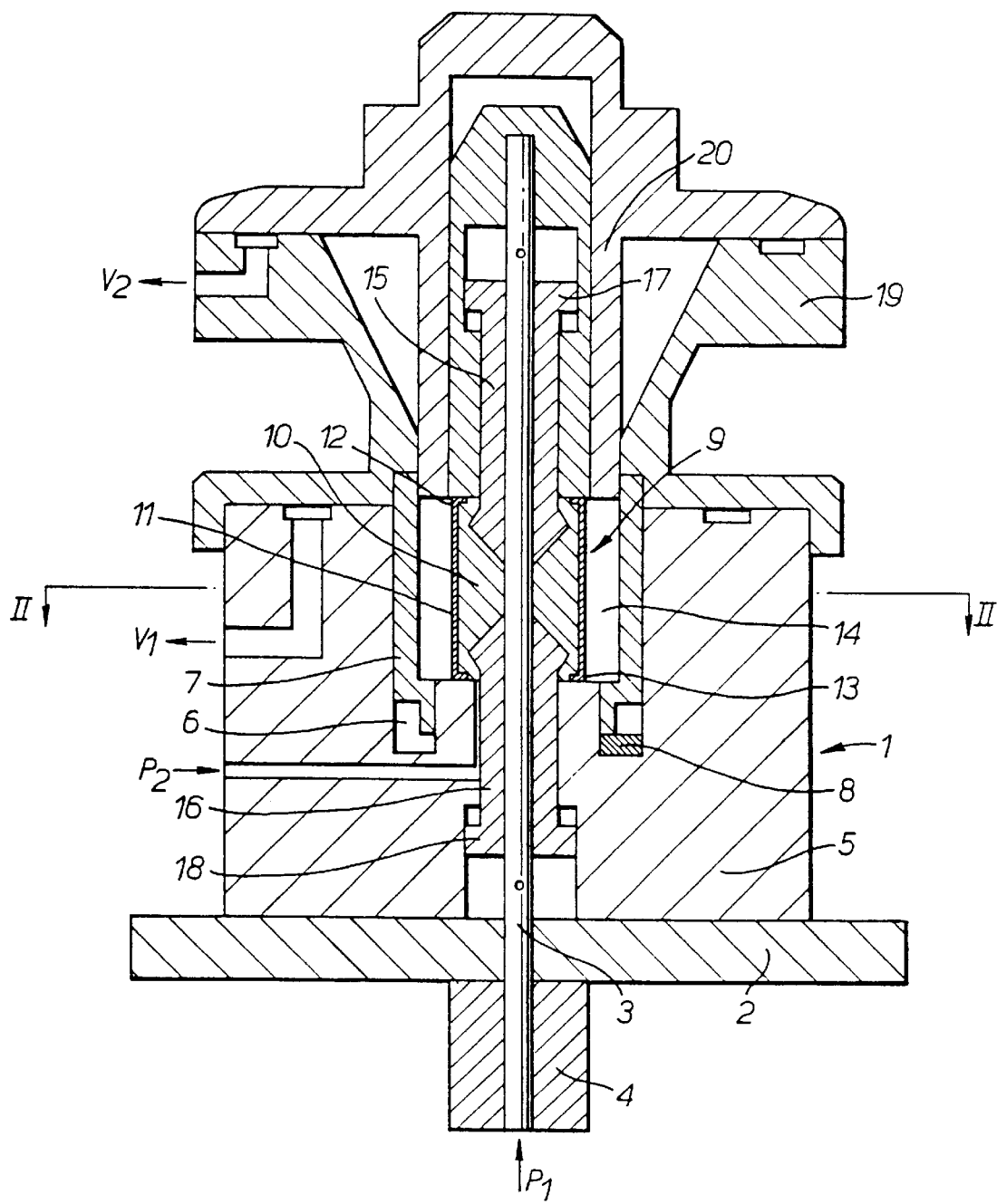
FIG. 1 is a longitudinal section of an apparatus for performing the process according to the invention.
Figure 2:
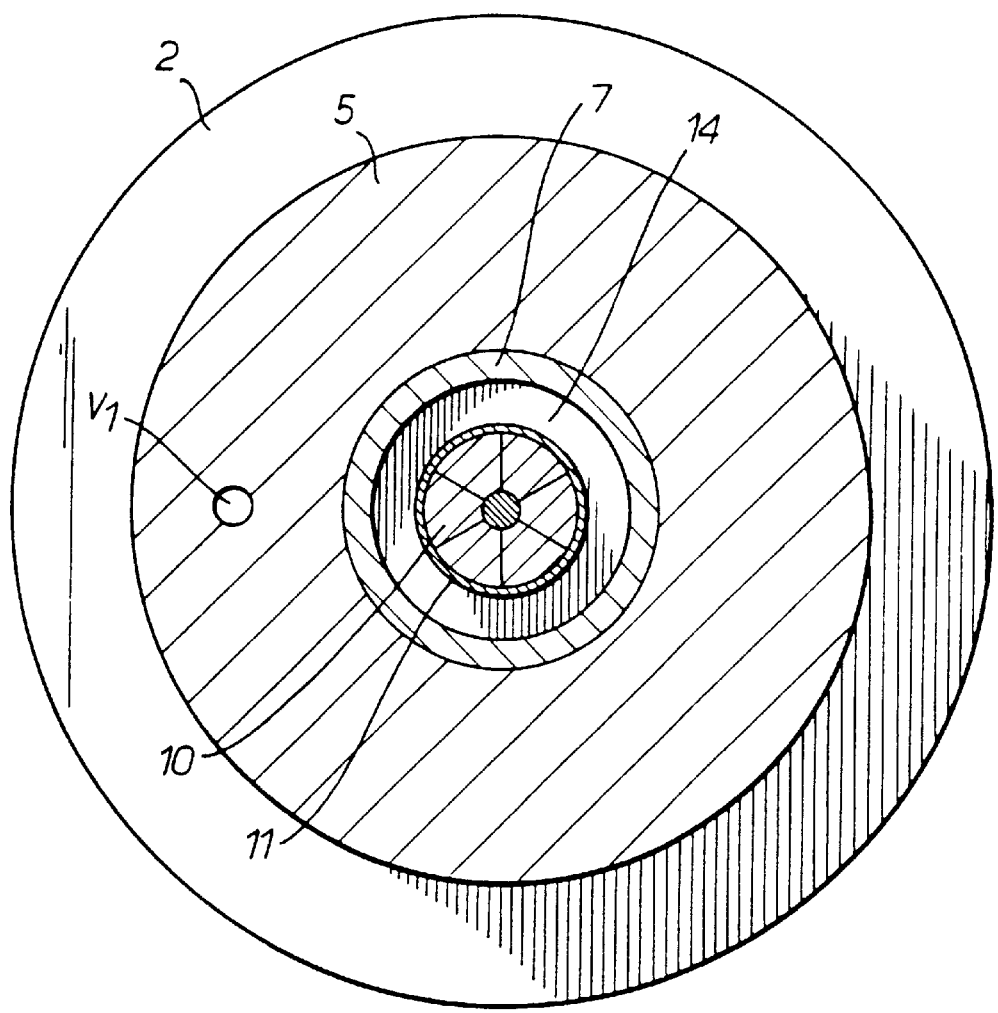
FIG. 2 is a sectional view on the line II—II of FIG. 1.

Referring firstly to FIGS. 1 and 2: the compaction apparatus (1) is supported on a base plate (2) which is mounted on a vibratory unit (not shown). A central shaft (3) is fitted into the base plate and locked in position by the housing (4) for air port ($P_1$). Housing (5) defining a cylindrical space (6) is fitted around central shaft (3). Moulding chamber (7) is supported within housing (5) on three radially spaced pegs, only one of which is illustrated, (8).

A cylindrical expansible mandrel (9) comprising six radially moveable segments (10) is positioned on central shaft (3). A cylindrical elastomeric sleeve (11) is fitted over segments (10). The ends of elastomeric sleeve (11) have a protruding lip (12, 13) which fits over the ends of segments (10), this helps to prevent uneven thinning of the sleeve (11) during expansion of the mandrel (9). The inner surface of moulding chamber (7) and the outer surface of the elastomeric sleeve (11) define the sides of the annular space (14) within which the medicament is compacted.

Pistons (15, 16) are slidably mounted on central shaft (3) and are driven by pressure differences across the piston heads (17, 18). The pistons (15, 16) slide against the inside of the segments (10) to achieve expansion of the mandrel.

Funnel (19) is removably attached to the top of housing (5) and can be clamped to the upper surface of the housing (5) under the action of vacuum ($V_1$).

Shroud (20), which provides the upper limiting face for compacting space (15), is removably attached to the upper surface of the housing (5) and can be held in position under the action of vacuum ($V_2$).

Figure 3:
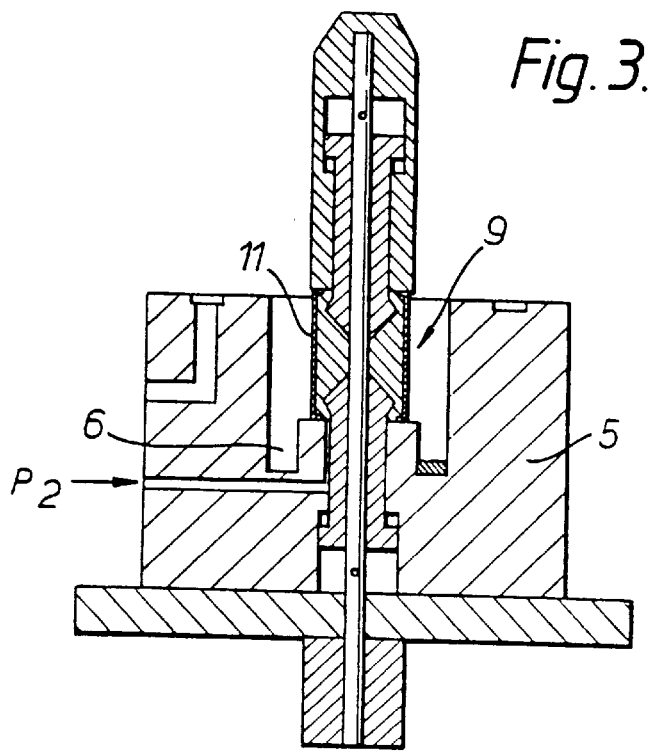
FIGS. 3 to 8 schematically show the production of a medicament compact according to the process of the invention.

Referring now to FIGS. 3 to 8 which illustrate the production of a medicament compact:

The expansible mandrel (9) is positioned along the longitudinal axis of the inner space (6) within housing (5) and a low pressure, e.g. 0.5 bar, is applied to air port ($P_2$) to give a positive pressure inside the elastomeric sleeve (11)—FIG. 3.

Figure 4:
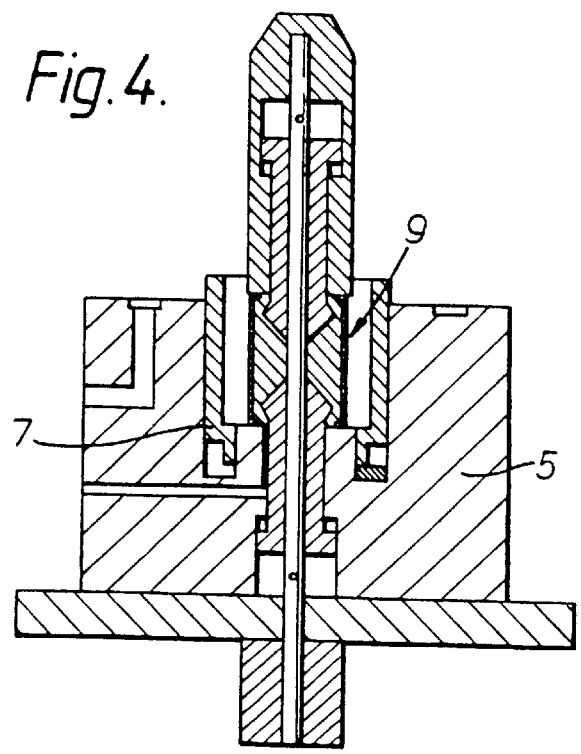

Moulding chamber (7) defining a cylindrical inner space is then fitted into housing (5) over the expansible mandrel (9)—FIG. 4.

Figure 5:
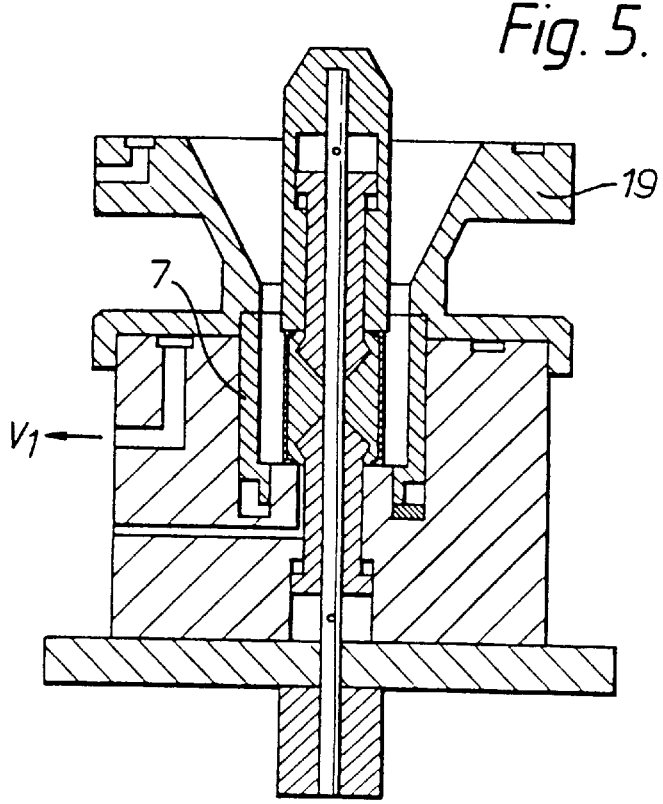
Figure 6:
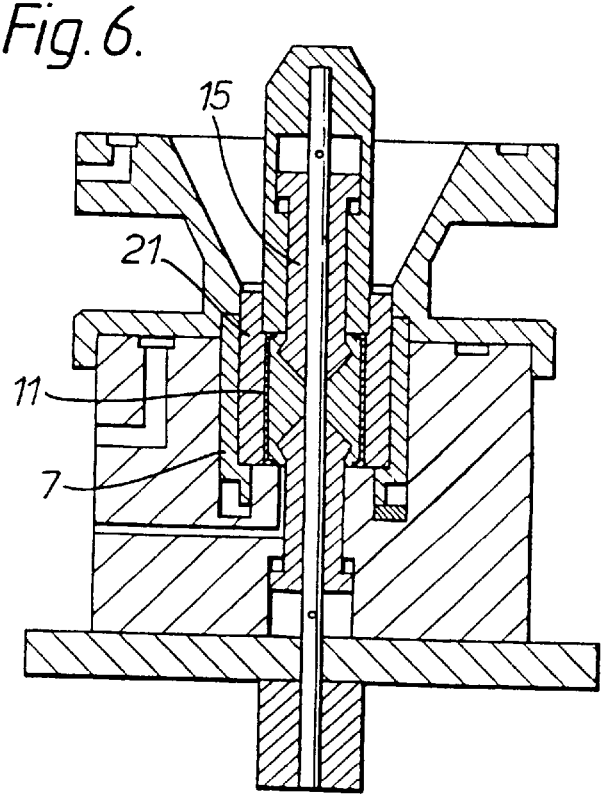
Figure 7:
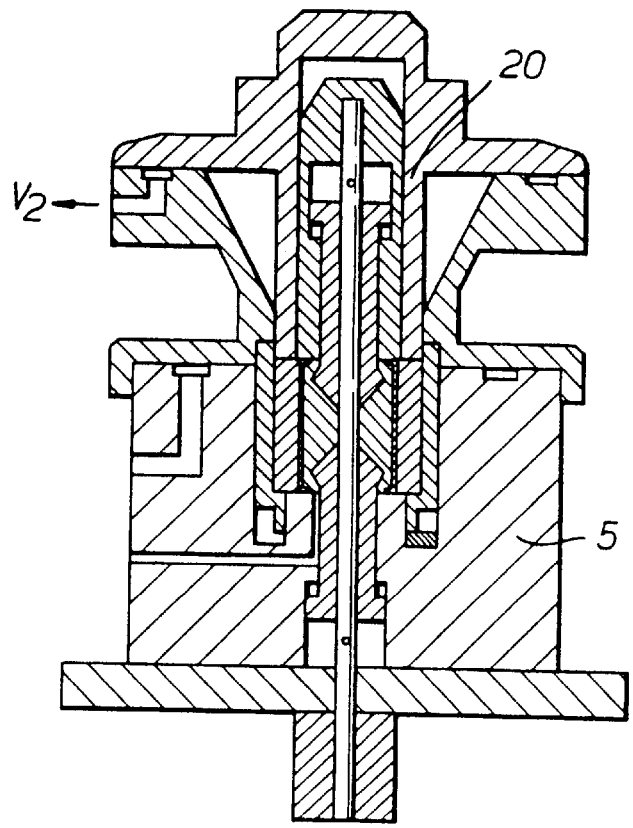
Figure 8:
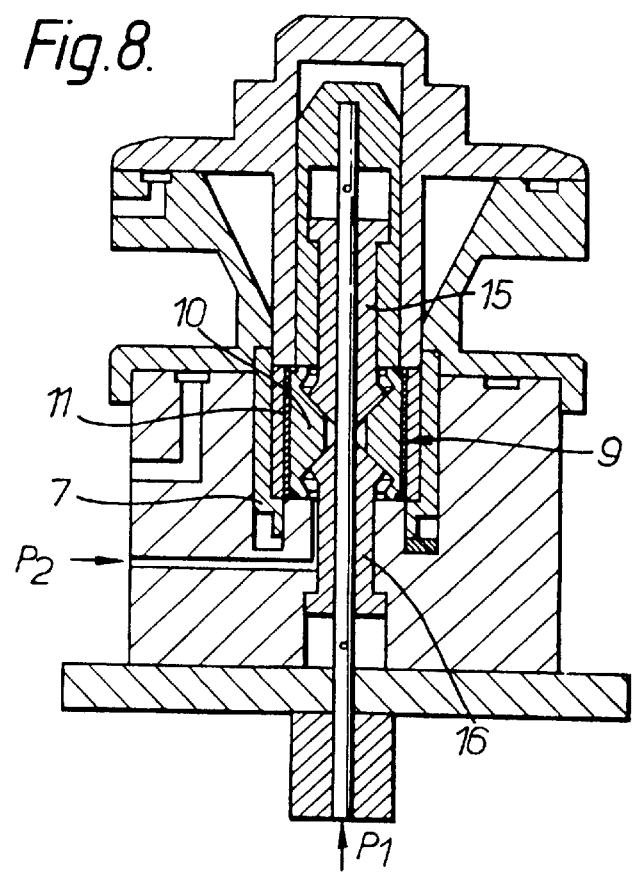

Filling funnel (19) is fitted onto the moulding chamber (7) and vacuum ($V_1$) is turned on—FIG. 5.

The vibratory system (not shown) is switched on and a known mass of loose powdered medicament (21) is metered into compacting space (14) between the elastomeric sleeve (11) and moulding chamber (7). The moulding chamber (7) is then vibrated until the powder settles to its "tapped density"—FIG. 6.

Shroud (20) is then fitted onto the housing (5) and allowed to drop onto the surface of the powder. The vibratory system is switched off and vacuum ($V_2$) turned on to clamp shroud (20) in position—FIG. 7.

High pressure, e.g. 10 bar, is applied to central shaft (3) via air port ($P_1$) thus increasing the air pressure behind piston heads (17, 18) and driving pistons (15, 16). The pistons (15, 16) slide against the inside of segments (10) and expand mandrel (9), thus reducing the radial separation of elastomeric sleeve (11) from the walls of moulding chamber (7) and compacting the medicament. The air pressure applied to the air port ($P_2$) is then increased, e.g. to 5 bar, to inflate the elastomeric sleeve (11) and make the powder compact more circular—FIG. 8.

The air supply ($P_1$) is then turned off reducing the pressure on pistons (15, 16) and the internal pressure applied to air port ($P_2$) reduced to e.g. 0.5 bar. Both vacuum supplies ($V_1$, $V_2$) are also turned off. The shroud (20) and funnel (19) are then removed, leaving the medicament compact (22) in moulding chamber (7). Moulding chamber (7) with medicament compact (22) therein may then be removed from the housing (5) and assembled directly into a medicament inhalation device.

Figure 9A:
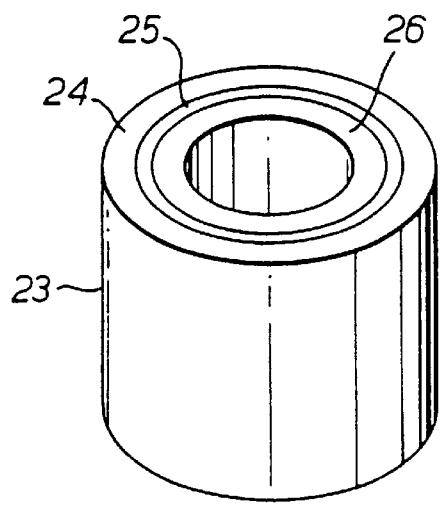
FIGS. 9a) and 9b) show perspective views of different medicament compacts produced according to the invention.

FIGS. 9a) and 10a) show a medicament compact (23) suitable for use in combination therapy. Three consecutive radial compressions are used to form an annulus of drug A (24), followed by an annulus of lactose (25), and finally an annulus of drug B (26).

Figure 9B:
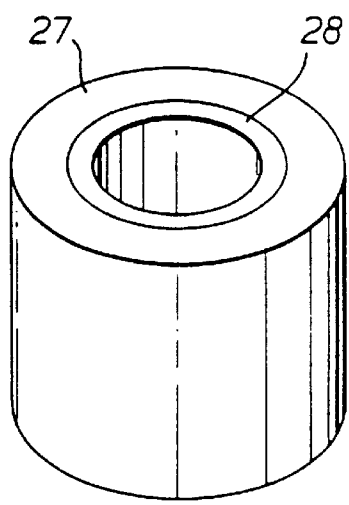
Figure 10A:
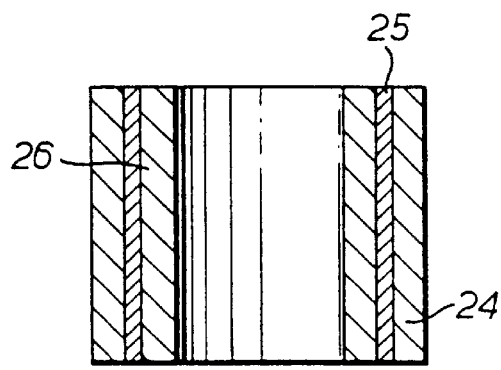
FIGS. 10a) and 10b) show vertical sections of the medicament compacts of FIGS. 9a) and 9b) respectively.
Figure 10B:
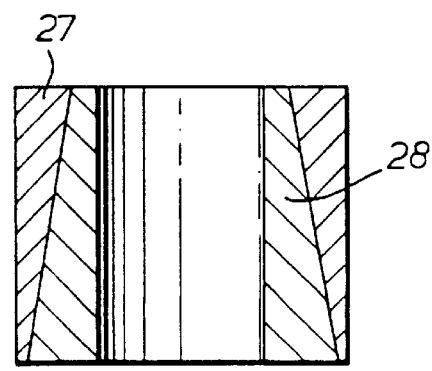

FIGS. 9b) and 10b) show a medicament compact where the dose of drug gradually increases on passing down the medicament compact. A tapered expansible means is used to form a tapered annulus of the carrier lactose (27), followed by a non-tapered expansible means to form an annulus of drug A (28).

We claim:

1. A process for the production of an inhalation medicament compact, which comprises the steps of:
    a) providing a mold having a longitudinal axis;
    b) positioning expansible means along said longitudinal axis, said mold forming all or part of the medicament reservoir of a medicament inhalation device;
    c) placing loose powdered medicament in the mold; and
    d) expanding the expansible means perpendicularly to the longitudinal axis of the mold.

2. A process according to claim 1, wherein the expansible means is an expansible mandrel.

3. A process according to claim 2, wherein the expansible mandrel is a cylindrical mandrel comprising a plurality of segments capable of radial movement.

4. A process according to claim 3, wherein the compact produced by the process has a longitudinal axis and the mandrel has the same number of segments as there are doses in a 360° rotation about said longitudinal axis of the compact.

5. A process according to claim 3, wherein the mandrel has from 2 to 12 segments.

6. A process as claimed in claim 3, wherein the diameter of the mandrel expands from 16 to 20 mm.

7. A process according to claim 1, wherein the expansible means is covered by an elastomeric sleeve.

8. A process according to claim 7, wherein the elastomeric sleeve comprises a natural rubber or a silicon rubber compound.

9. A process according to claim 7, wherein the elastomeric sleeve is constructed and arranged to be inflated relative to the expansible means.

10. A process according to claim 1, wherein the expansible means is expanded by the action of air driven pistons.

11. A process according to claim 1, wherein the expansible means comprises an inflatable bag.

12. A process as claimed in claim 1, wherein after or during step (c) the medicament is settled to a level height.

13. A process as claimed in claim 12, wherein the medicament is settled by vibration of the mold.

14. A process as claimed in claim 1, wherein the expansible means exerts a pressure of from $60 \times 10^3$ to $2000 \times 10^3$ N m$^{-2}$.

15. A process as claimed in claim 1, wherein the compact produced is packaged to provide a replacement medicament reservoir for an inhalation device from which the medicament is to be administered.

16. A process as claimed in claim 1, wherein the active ingredient is selected from the group consisting of cromoglycic acid; salts of nedocromil; inhaled steroids; anticholinergic agents; bronchodilators and salts thereof; antihistamines; peptide hormones; bradykinin antagonists; $PLA_2$ inhibitors; PAF antagonists; glutamate antagonists; CK antagonists and agonists; macrolide compounds; vitamins; vaccines; and vectors for gene therapy.

17. A process as claimed in claim 1, wherein medicament compacts are formed comprising concentric annuli of different active ingredients or carrier substances.

18. An apparatus for the production of an inhalation medicament compact from loose powdered inhalation medicament which comprises:
   a) a mold, having a longitudinal axis for receiving loose powdered medicament, said mold forming all or part of the medicament reservoir of a medicament inhalation device;
   b) expansible means positionable along the longitudinal axis of the mold; and
   c) means for expanding the expansible means perpendicularly to the longitudinal axis of the mold.

19. Apparatus as claimed in claim 18 and further comprising a vibrator or leveling device to settle the medicament to a level height.

20. A process as claimed in claim 1, wherein medicament compacts are formed having a density at a given radius from the longitudinal axis of said compact that is the same throughout its length.

21. A process for the production of an inhalation medicament compact having annuli of different active ingredients or carrier substances, which comprises the steps of:
   a) providing a mold having a longitudinal axis;
   b) positioning expansible means along said longitudinal axis;
   c) placing loose powdered medicament in the mold; and
   d) expanding the expansible means perpendicularly to the longitudinal axis of the mold to produce a medicament compact such that the density of said compact at a given radius from the longitudinal axis of said compact is the same throughout its length and such that annuli of different active ingredients or carrier substances are formed.

22. A process according to claim 21, wherein the expansible means is an expansible mandrel.

23. A process according to claim 22, wherein the expansible mandrel is a cylindrical mandrel comprising a plurality of segments capable of radial movement.

24. A process according to claim 23, wherein the compact produced by the process has a longitudinal axis and the mandrel has the same number of segments as there are doses in a 360° rotation about said longitudinal axis of the compact.

25. A process according to claim 21, wherein the expansible means is covered by an elastomeric sleeve.

26. A process according to claim 25, wherein the elastomeric sleeve comprises a natural rubber or a silicon rubber compound.

27. A process according to claim 25, wherein the elastomeric sleeve is constructed and arranged to be inflated relative to the expansible means.

28. A process according to claim 21, wherein the expansible means is expanded by the action of air driven pistons.

29. A process according to claim 21, wherein the expansible means comprises an inflatable bag.

30. A process according to claim 23, wherein the mandrel has from 2 to 12 segments.

31. A process according to claim 21, wherein after or during step (c) the medicament is settled to a level height.

32. A process according to claim 31, wherein the medicament is settled by vibration of the mold.

33. A process according to claim 23, wherein the diameter of the maridrel expands from 16 to 20 mm.

34. A process according to claim 21, wherein the expansible means exerts a pressure of from $60 \times 10^3$ to $2000 \times 10^3$ $Nm^{-2}$.

35. A process according to claim 21, further including the step of packaging the compact produced to provide a replacement medicament reservoir for an inhalation device from which the medicament is to be administered.

36. A process according to claim 21, wherein the active ingredient is selected from the group consisting of cromoglycic acid; salts of nedocromil; inhaled steroids; anticholinergic agents; bronchodilators and salts thereof; antihistamines; peptide hormones; bradykinin antagonists; $PLA_2$ inhibitors; PAF antagonists; glutamate antagonists; CK antagonists and agonists; macrolide compounds; vitamins; vaccines; and vectors for gene therapy.

* * * * *